United States Patent
Bartula et al.

(10) Patent No.: US 10,521,900 B2
(45) Date of Patent: Dec. 31, 2019

(54) CAMERA FOR GENERATING A BIOMETRICAL SIGNAL OF A LIVING BEING

(75) Inventors: Marek Janusz Bartula, Eindhoven (NL); Willem Verkruijsse, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 689 days.

(21) Appl. No.: 14/240,048

(22) PCT Filed: Aug. 27, 2012

(86) PCT No.: PCT/IB2012/054375
§ 371 (c)(1),
(2), (4) Date: Feb. 21, 2014

(87) PCT Pub. No.: WO2013/030745
PCT Pub. Date: Mar. 7, 2013

(65) Prior Publication Data
US 2014/0192177 A1 Jul. 10, 2014

Related U.S. Application Data

(60) Provisional application No. 61/530,546, filed on Sep. 2, 2011.

(51) Int. Cl.
*G06T 7/00* (2017.01)
*A61B 5/024* (2006.01)
*A61B 5/1455* (2006.01)

(52) U.S. Cl.
CPC ........ *G06T 7/0012* (2013.01); *A61B 5/02427* (2013.01); *A61B 5/14551* (2013.01);
(Continued)

(58) Field of Classification Search
CPC ................. G06T 7/0012; G06T 7/0016; G06T 2207/10024; G06T 2207/30076; A61B 5/02427; A61B 5/14551
(Continued)

(56) References Cited

U.S. PATENT DOCUMENTS 5,555,464 A * 9/1996 Hatlestad ............ A01M 7/0089
348/266
6,775,565 B1 * 8/2004 Wieringa ............. A61B 5/1455
600/322
(Continued)

FOREIGN PATENT DOCUMENTS

| JP | 61-151705 | 10/1986 |
| JP | H02172443 | 7/1990 |

(Continued)

OTHER PUBLICATIONS

Humphreys, K., et al.; Noncontact simultaneous dual wavelength photoplethysmography: A further step toward noncontact pulse oximetry; 2007; Review of Scientific Instruments; 78:044304-1-6.
(Continued)

*Primary Examiner* — William C Vaughn, Jr.
*Assistant Examiner* — Daniel T Tekle

(57) ABSTRACT

The present invention relates to a camera (1, 1') for generating a biometrical signal of a living being comprising: a filter (11) for blocking incident visible light in a wavelength range up to at least 550 nm, a color sensor (12, 12') for receiving said filtered incident light and generating at least two different color signals (5, 6, 9), a combination unit (15) for generating at least one combined color signal (7a, 7b) by combining said at least two color signals, and a processing unit (16) for processing said at least one combined color signal and extracting at least one biometrical signal (8) of said living being (3).

10 Claims, 8 Drawing Sheets

(52) U.S. Cl.
CPC .. *G06T 7/0016* (2013.01); *G06T 2207/10024* (2013.01); *G06T 2207/30076* (2013.01)

(58) Field of Classification Search
USPC .......................................................... 348/77
See application file for complete search history.

(56) References Cited

U.S. PATENT DOCUMENTS

| | | | |
|---|---|---|---|
| 7,235,775 | B2 | 6/2007 | Masaki |
| 2003/0163032 | A1 | 8/2003 | Terry |
| 2005/0027166 | A1* | 2/2005 | Matsumoto ............ A61B 1/041 600/162 |
| 2008/0306372 | A1 | 12/2008 | Ohki et al. |
| 2009/0280859 | A1* | 11/2009 | Bergh ............... G06F 17/30256 455/556.1 |
| 2009/0306487 | A1 | 12/2009 | Crowe et al. |
| 2011/0066062 | A1* | 3/2011 | Banet ................. A61B 5/0402 600/534 |
| 2011/0112385 | A1* | 5/2011 | Aalders ............... A61B 5/0059 600/322 |
| 2012/0212361 | A1* | 8/2012 | Lai ........................... H03K 5/24 341/143 |
| 2012/0212631 | A1* | 8/2012 | Klirenko .............. A61B 5/0059 348/207.1 |

FOREIGN PATENT DOCUMENTS

| | | |
|---|---|---|
| JP | 2001346768 A | 12/2001 |
| JP | 2005218507 A | 8/2005 |
| JP | 2008142150 A | 6/2008 |
| JP | 2009106680 A | 5/2009 |
| WO | 0115597 A1 | 3/2001 |
| WO | 2011042839 A1 | 4/2011 |
| WO | 2011055288 A1 | 5/2011 |

OTHER PUBLICATIONS

Mohan, N. M., et al.; Contact-less, Multi-Spectral Imaging of Dermal Perfusion; 2008; Instrumentation and Measurement Technology Conf.; pp. 793-796.

Sahindrakar, P.; Improving Motion Robustness of Contactless Monitoring of Heart Rate Using Video Analysis; 2011; Technische Universiteit Eindhoven; retrieved from the Internet: http://alexandria.tue.nl/extra1/afstversl/wsk-i/sahindrakar2011.pdf.

* cited by examiner

CAMERA FOR GENERATING A BIOMETRICAL SIGNAL OF A LIVING BEING

CROSS REFERENCE TO RELATED APPLICATIONS

This application is a national filing of PCT application Serial No. PCT/IB2012/054375, filed Aug. 27, 2012, published as WO 2013/030745 A1 on Mar. 7, 2013, which claims the benefit of U.S. provisional application Ser. No. 61/530,546 filed Sep. 2, 2011, which is incorporated herein by reference.

FIELD OF THE INVENTION

The present invention relates to a camera for generating a biometrical signal of a living being. The present invention relates further to a method for generating a biometrical signal of a living being. Still further, the present invention relates to a processor and a processing method for use in such a camera and method. Finally, the present invention relates to a computer program for implementing said processing method.

BACKGROUND OF THE INVENTION

Pulse oximetry is a non-invasive method allowing a monitoring of the oxygenation of a patient's hemoglobin using a pulse oximeter. A sensor is placed on a thin part of a patient's body, usually a finger tip or earlobe. Red light with a wavelength around 650 nm and infrared light with a wavelength around 850 to 940 nm are sequentially passed through the patient to a photodetector. The changing absorbance of each of the two wavelengths is measured, allowing determination of the absorbances due to the pulsing arterial blood alone, excluding venous blood, skin, bone, muscle and fat. Based upon the ratio of changing absorbance of the red and infrared light caused by the difference in color between oxygen-bound (bright red) and oxygen-unbound (dark red or blue in severe cases) blood hemoglobin, a measure of oxygenation (the percent of hemoglobin molecules bound with oxygen molecules) can be made. This is also called SpO2 monitoring in the art.

Camera-based SpO2 monitoring is conventionally realized by two monochrome cameras with corresponding optical band-pass filters, but this is non-practical due to the required alignment (i.e. spatial alignment of the images from two or more sensors), complexity and costs for many applications, such as applications in sports, home-use or for implementation in smart devices, such as mobile phones.

SUMMARY OF THE INVENTION

It is an object of the present invention to provide a camera and a corresponding method for generating a biometrical signal of a living being that can be applied in a wider range of applications and that are less complex and expensive compared to conventional camera-based monitoring equipment and methods. It is a further object of the present invention to provide a corresponding processor and processing method for use in such a camera as well as a computer program for implementing said processing method.

In a first aspect of the present invention a camera is presented comprising:

a filter for blocking incident visible light in a wavelength range up to at least 550 nm, in particular up to at least 600 nm, a color sensor for receiving said filtered incident light and generating three different color signals, a combination unit for generating at least one combined color signal by combining said at least two color signals, and a processing unit for processing said at least one combined color signal and extracting at least one biometrical signal of said living being.

In a further aspect of the present invention a processor for use in a camera for generating a biometrical signal of a living being is presented comprising:

a combination unit for generating at least one combined color signal by combining said at least two color signals, and a processing unit for processing said at least one combined color signal and extracting at least one biometrical signal of said living being.

In a further aspect of the present invention corresponding methods are presented as well as a computer program comprising program code means for causing a computer to carry out the steps of the processing method when said computer program is carried out on the computer.

Preferred embodiments of the invention are defined in the dependent claims. It shall be understood that the claimed method has similar and/or identical preferred embodiments as the claimed device and as defined in the dependent claims.

The present invention is based on the idea to add a special filter to a camera for generating a biometrical signal (also called vital sign) of a living being. While in conventional cameras a filter is used that blocks incident infrared light so that mainly visible light is sensed by a color sensor, e.g. an RGB sensor, according to the present invention quite the contrary is proposed and a filter is used that blocks incident visible light in a wavelength range up to at least 550 nm, preferably up to at least 600 nm. In other words, the spectral characteristics of the camera are modified by placing a filter for blocking incident visible light in the optical path of the camera so that only light above a certain threshold wavelength hits the color sensor.

The color sensor generates at least two different color signals. These color signals are combined into at least one combined color signal which is then further processed to extract the desert biometrical signal. The result is an inexpensive and rather simple camera with near optimal spectral characteristics for biometrical signal detection, in particular for SpO2 monitoring and SpO2 imaging.

The invention is, however, not restricted to the detection of an SpO2 signal, but may also extract other biometrical signals, such as heart beat, cardiac cycle, respiratory rate, depth of anesthesia or hypo- and hypervolemia of the living being. For instance, heart beat (also called heart rate or HR) detection from the at least one combined color signal is more robust with the proposed camera and method and can even be done under near dark illumination conditions since, according to the present invention, mainly the infrared light is evaluated rather than visible light as is conventionally done.

In a preferred embodiment the color sensor is adapted for generating three different color signals, preferably a red color signal, a green color signal and a blue color signal. Of course, these color sensors also have a sensitivity in the infrared wavelength range. The color sensor is preferably a standard RGB sensor including a photo detector and a color filter array for filtering the incident light differently before hitting the photo detector. In another embodiment the color sensor comprises a separate (different) color detectors for detecting different spectral parts of the incident light and generating different color signals.

In general, CCD/CMOS sensor manufacturers offer such sensors in monochrome (i.e. without color filters) and RGB (i.e. with a color filter array "printed" on top of the pixels) versions. The spectral response of those filters is optimized for the visible band. Increasing transparency of green and blue filters in near-infrared band (where the silicon of the sensor is still sensitive) is a side effect of the used chemicals (dyes). It is normally solved by equipping color cameras with IR-block filters by default.

The present invention can thus also be understood as a kind of misuse of such color sensors, in particular RGB color sensors (and their undesired behavior in the near infra-red spectral range) trying to obtain a signal that would otherwise require different custom made optical filters.

The main reason for preferably using a standard, commercially available RGB sensor, is a cost factor (these sensors are made in huge volumes). Custom made color arrays are expensive when manufactured in low numbers. Using more than one monochrome sensor with optical filters, which is generally possible as well, but increases the total system cost as well. Additionally, it introduces spatial alignment and/or perspective problems of the images from different sensors.

In another preferred embodiment the combination unit is adapted for combining said at least two color signals by a linear combination. Linear combinations have been shown to provide good results. But in certain circumstances, in particular dependent on the kind of color sensor and/or the spectrum of the light source illuminating the living being, other combinations might be used alternatively.

In another embodiment the combination unit is adapted for generating two combined color signals by making two different combinations, in particular linear combinations, of at least two of said three generated color signals. A good combination is a combination that minimizes cross-talk between said at least two combined color signals and thus maximizing contrast in the resulting biometrical signal. For instance, if the biometrical signal is extracted from the combined color signals by PPG (photoplethysmography) extraction the contrast between PPG amplitudes may thus be maximized.

A preferred combination leading to good results generates a first combined color signal by adding the red color signal and the green color signal and subtracting two times the blue color signal from said sum and generates a second combined color signal by subtracting the green color signal from two times the blue color signal.

In another embodiment said filter is adapted for blocking incident visible light in a wavelength range up to at least 650 nm. Generally, blue and green color detectors have a local minimum in light transmission in the wavelength range around 650 nm. It is preferred to block, however, a green sensitivity peak in the visible spectrum which is generally centered around 545 nm. A threshold at a longer wavelength above 650 nm is not preferred since this would reduce the contrast for the biometrical signal detection. Those biometrical signals generally have minima in a wavelength range around 660 nm which thus represents a wavelength range in which the detection of the biometrical signal or the evaluation of a biometrical signal can best be done.

Naturally, in imaging silicon sensors, as preferably used in the color sensor, the sensitivity decreases towards longer wavelengths. If, however, this is not the case for a certain color sensors another filter may be placed in the optical path of the camera that blocks incident light in a wavelength range above at least 1100 nm, in particular above at least 1000 nm, before reaching said color sensor.

As mentioned above, the proposed camera may be used for generating different kinds of biometrical signals. One field of a preferred application of the present invention is for extracting a heart beat signal from that at least one combined color signal by PPG extraction.

A method to measure skin colour variations, called Photo-Plethysmographic imaging (PPG), is described in Wim Verkruysse, Lars O. Svaasand, and J. Stuart Nelson, "Remote plethysmographic imaging using ambient light", Optics Express, Vol. 16, No. 26, December 2008. It is based on the principle that temporal variations in blood volume in the skin lead to variations in light absorptions by the skin. Such variations can be registered by a video camera that takes images of a skin area, e.g. the face, while processing calculates the pixel average over a manually selected region (typically part of the cheek in this system). By looking at periodic variations of this average signal, the heart beat rate and respiratory rate can be extracted.

Thus, the pulsation of arterial blood causes changes in light absorption. Those changes observed with a photodetector (or an array of photodetectors) form a PPG (photoplethysmography) signal (also called, among other, a pleth wave). Pulsation of the blood is caused by the beating heart, i.e. peaks in the PPG signal correspond to the individual beats of the heart. Therefore, a PPG signal is a heartbeat signal in itself. The normalized amplitude of this signal is different for different wavelengths, and for some wavelengths it is also a function of blood oxygenation.

To improve robustness of heart rate calculation, it is beneficial to use more than one PPG signal, in particular signals obtained at different wavelengths in such a way, that the difference of normalized amplitudes is maximized. Division of one signal by the other helps to eliminate distortions present in both signals.

Another field of application of the present invention is SpO2 estimation. Thus, preferably, the processing means is adapted for extracting a SpO2 signal from said at least one combined color signal by extracting at least two PPG signals at different wavelengths and determining a SpO2 signal from said at least two PPG signals.

SpO2 estimation is based on the ratio of the normalized amplitudes of PPG signal at two different ranges of wavelengths (one at red and the other at infra-red part of the spectrum):

$$RR = \frac{\frac{AC_{IR}}{DC_{IR}}}{\frac{AC_R}{DC_R}}.$$

From this "ratio of ratios", the SpO2 value is obtained using experimentally defined constants $C_1$ and $C_2$ $$SpO_2 = C_1 - \frac{C_2}{RR}.$$

The biometrical signal being directly measured is the PPG signal. SpO2 is calculated from two PPG signals. Similarly, other mentioned signals/properties (respiration, depth of anesthesia, etc.) are also derivatives of the PPG signal.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
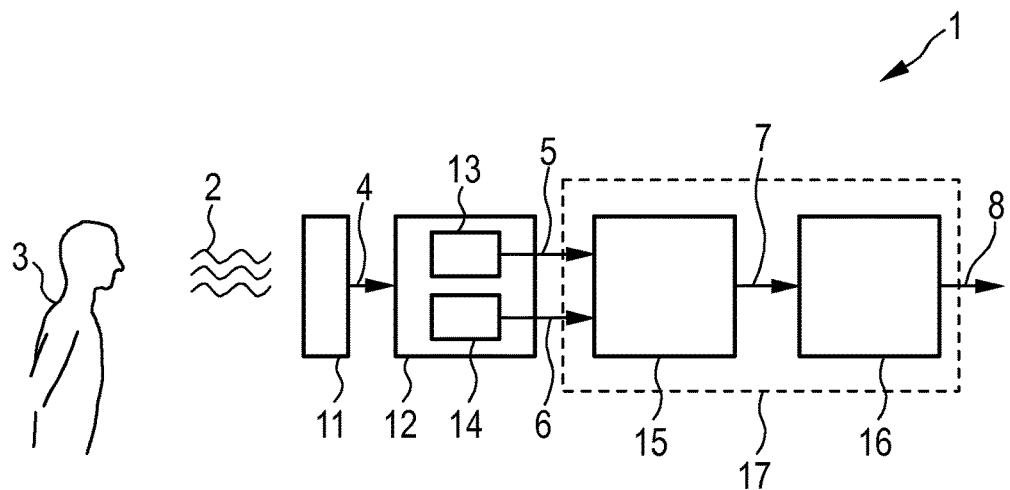
FIG. 1 shows a schematic diagram of a camera according to the present invention.

FIG. 1 shows a schematic diagram of a first embodiment of a camera 1 according to the present invention. Electromagnetic radiation 2, in particular light in the visible and infrared wavelength range, reflected from a living being 3, such as a patient, is received and evaluated by said camera 1 for finally generating the biometrical signal of the living being 3. The camera comprises a filter 11 for blocking incident visible light within the incident electromagnetic radiation 2 in a wavelength range up to at least substantially 550 nm, preferably up to approximately 600 nm, even more preferably up to 650 nm. The filtered incident light 4 is then sensed by a color sensor 12 that generates at least two different color signals 5, 6, e.g. by use of two separate color detectors 13, 14 (or an array of such color detectors). A combination unit 15 generates at least one combined color signal 7 by combining said color signals 5, 6, e.g. by a linear combination. Finally, a processing unit 16 is provided for processing said combined color signal 7 and extracting at least one biometrical signal 8 of the living being 3.

The combination unit 15 and the processing unit 16 are preferably realized at a common processor 17, e.g. are realized as processing elements of a processor or are implemented in software on a conventional processor. However, they may also be realized in a different manner, e.g. as dedicated hardware elements.

Figure 2:
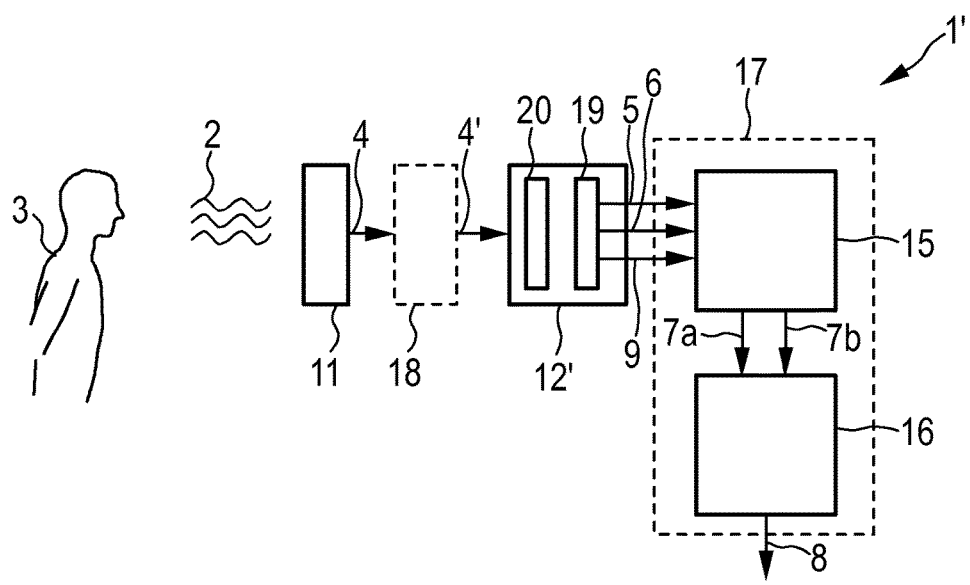
FIG. 2 shows a schematic diagram of another embodiment of a camera according to the present invention.

FIG. 2 schematically shows a second embodiment of a camera 1' according to the present invention. FIG. 2 shows that optionally an additional filter 18 may be provided (in this and/or other embodiments), which filter 18 is configured to block incident light in a wavelength range above at least 1100 nm, in particular above at least 1000 nm, before reaching the color sensor 12'. While generally those color sensors, e.g. imaging silicon sensors, show a sensitivity that naturally decreases towards longer wavelengths, such an additional filter 18 ensures that signal contributions within the filtered incident light 4 above said upper threshold wavelength are blocked, i.e. signal contributions in which water absorption becomes dominant are blocked in the twice filtered incident light 4'.

Further, in this embodiment the color sensor 12' generates three different color signals 5, 6, 9, e.g. by use of a color filter array 20 having three different color filter areas provided in front of a photo detector 19 (or, more generally, the image sensor). Such a color sensor (e.g. including a color filter array having only two color filter areas could also be used in the embodiment shown in FIG. 1. Preferably, the color sensor 12' comprises a color filter array generating a red color signal 5, a green color signal 6 and a blue color signal 9 as conventionally provided by an RGB color sensor.

From the three color signals 5, 6, 9 the combination unit 15 generates two combined color signals 7a, 7b by making two different combinations, in particular linear combinations, of at least two of said three color signals 5, 6, 9. From these two combined color signals 7a, 7b the processing unit then finally extracts the desired biometrical signal 8.

Figure 3:
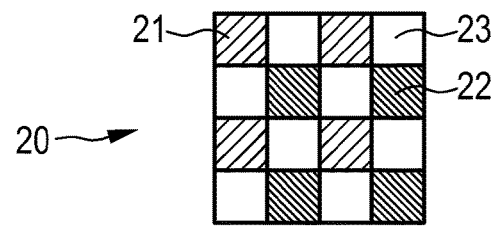
FIG. 3 shows a top view of a Bayer color filter array.

As explained above standard RGB cameras use a color filter array overlaid over pixels of the image sensor in a repetitive pattern. Such a Bayer color filter array 20 that can also be used according to the present invention is depicted in FIG. 3. Such a color filter array comprises a number of red filter areas 21, blue filter areas 22 and green filter areas 23. The spectral response is generally optimized for the visual representation of recorded images. However, such standard RGB cameras are far from optimal for camera-based generation of biometrical signals of a living being, in particular for camera-based PPG extraction including the extraction of heart rate signals and SpO2 signals. An option would be the use of custom-made color filter arrays, but these are generally an expensive alternative.

Further, conventionally an IR filter blocking infrared light is placed in front of the RGB camera to block infrared light. According to the present invention, instead, the visible light is blocked with the filter 11 up to a predetermined threshold wavelength, typically in the range from 550 to 650 nm (e.g. around 600 nm), and no extra infrared filter is generally used. A color sensor 12 is preferably a conventional color sensor, such as a standard RGB sensor as used in an RGB camera which, in an embodiment, may also include such a Bayer color filter array 20 as shown in FIG. 3 or any other means for providing at least two (preferably three) color signals.

Figure 4:
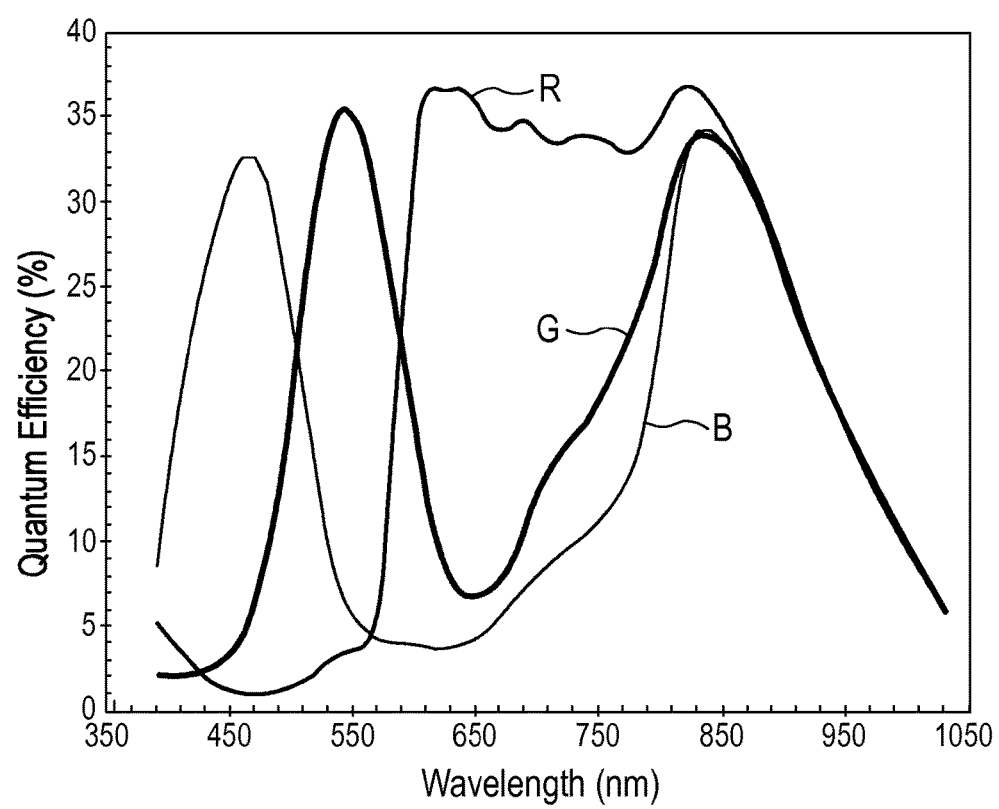
FIG. 4 shows a diagram illustrating the spectral characteristics of a conventional color sensor.
Figure 5:
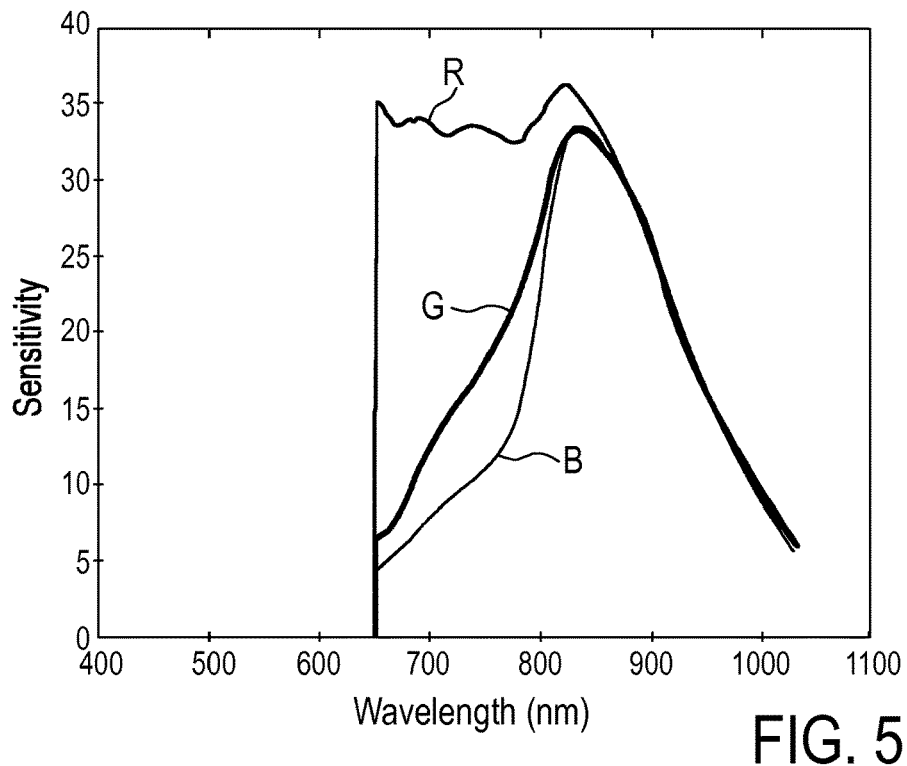
FIG. 5 shows the used spectral parts of three different color signals according to the present invention.

The effects of the present invention shall be illustrated by way of an example assuming the use of a conventional RGB camera sensor including a Bayer color filter array. The spectral characteristics of such a Bayer color filter array are depicted in FIG. 4 showing the sensitivity curve B for blue light, the sensitivity curve G for green light and the sensitivity curve R for red light. By default, conventional cameras are equipped with infrared block filters, as mentioned above, to block infrared light, particularly in the wavelength range above 650 nm, to avoid influence of light from outside the visible range. According to the present invention, however, such an IR block filter is removed and actually the visible part of the sensitivity spectrum is blocked up to a threshold wavelength in the range from 550 to 650 nm as depicted in the diagram shown in FIG. 5 showing only the part of the spectra that are passing through the filter unit 11.

Next, in the combination unit 15, from these three color signals R, G, B (representing the color signals 5, 6, 9 in this example) to combined color signals 7a, 7b are generated by linear combinations of the color signals. In particular, in an embodiment the first combined color signal Ch1 (e.g. representing combined color signal 7a) is defined as Ch1=R−

Figure 6:
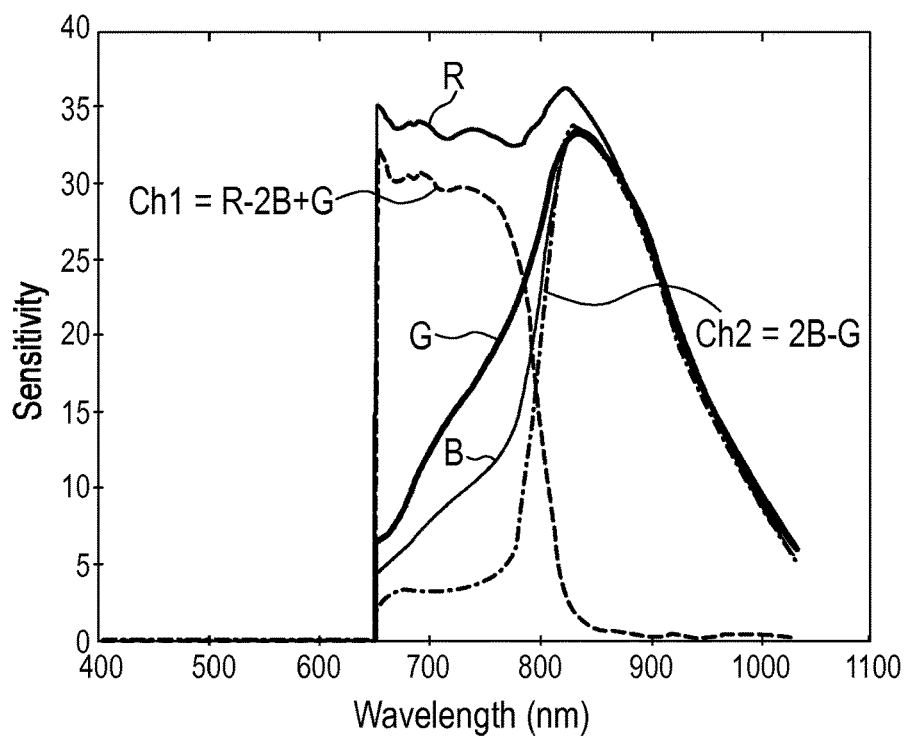
FIG. 6 shows the spectral sensitivities of two combined color signals generated according to the present invention.

2b+G and the second combined color signal Ch2 (representing the second combined color signal 7b) is defined as Ch2=2 B−G. The spectral sensitivities of combined color signals Ch1 and Ch2 are depicted in the diagram shown in FIG. 6. To be precise, this diagram does not show any signals, but a spectral sensitivity characteristic, where a signal is understood as a time varying value obtained by integration of light by those sensitivity curves.

Referring to the diagram shown in FIG. 4 showing an effective spectral characteristic of the color filter array and silicon sensitivity, which is generally the same for all pixels, it can be seen that going from a wavelength of 650 nm towards longer wavelengths, the filter areas of the color sensor more or less maintain their transmission level, while the blue and green filter areas of the color sensor are becoming more and more "transparent". At some wavelength around 830 nm the silicon sensitivity starts dropping down, which equally limits the light collection by all three color channels. Further, it can be seen that at a wavelength around 650 nm the blue and green filter areas have a local minimum in light transmission.

Figure 7:
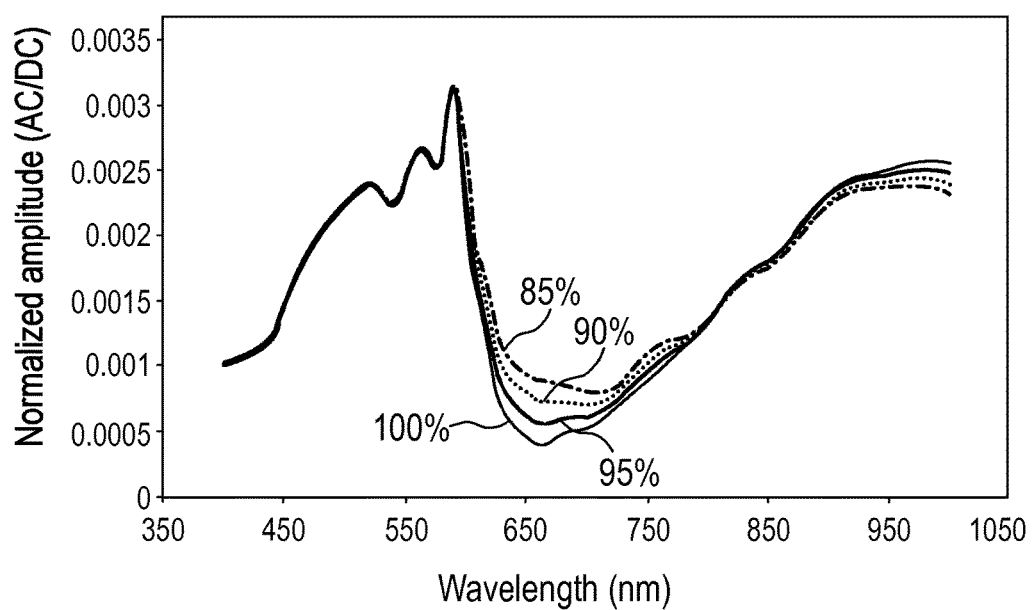
FIG. 7 shows a diagram illustrating the normalized amplitude over the PPG amplitude spectra for one person and different SpO2 saturation values.

According to the present invention, it has been shown that it is desired to block the green filter peak in the visible spectrum which is around 545 nm. On the other hand, to avoid a severe reduction of the contrast the upper threshold wavelength of the filter unit 11 should not be substantially higher than 700 nm, particularly not higher than 650 nm. The reason can be seen from the diagram shown in FIG. 7 showing PPG amplitude spectra for one person and different SpO2 saturation values from 85% to 100%. Since it is desired to capture the minima of these curves, which minima are around 660 nm, the upper threshold wavelength of the filter unit should not be above the wavelength of these minima.

Figure 8A:
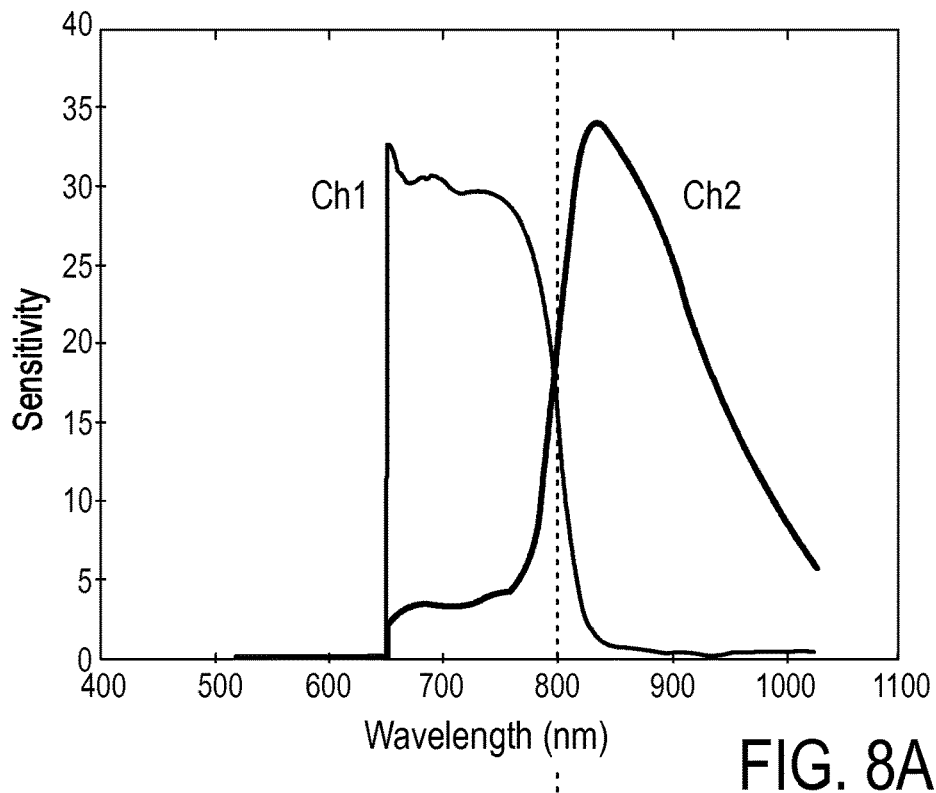
FIG. 8 shows diagrams for a sensitivity and normalized amplitude to illustrate SpO2 signal evaluation.
Figure 8B:
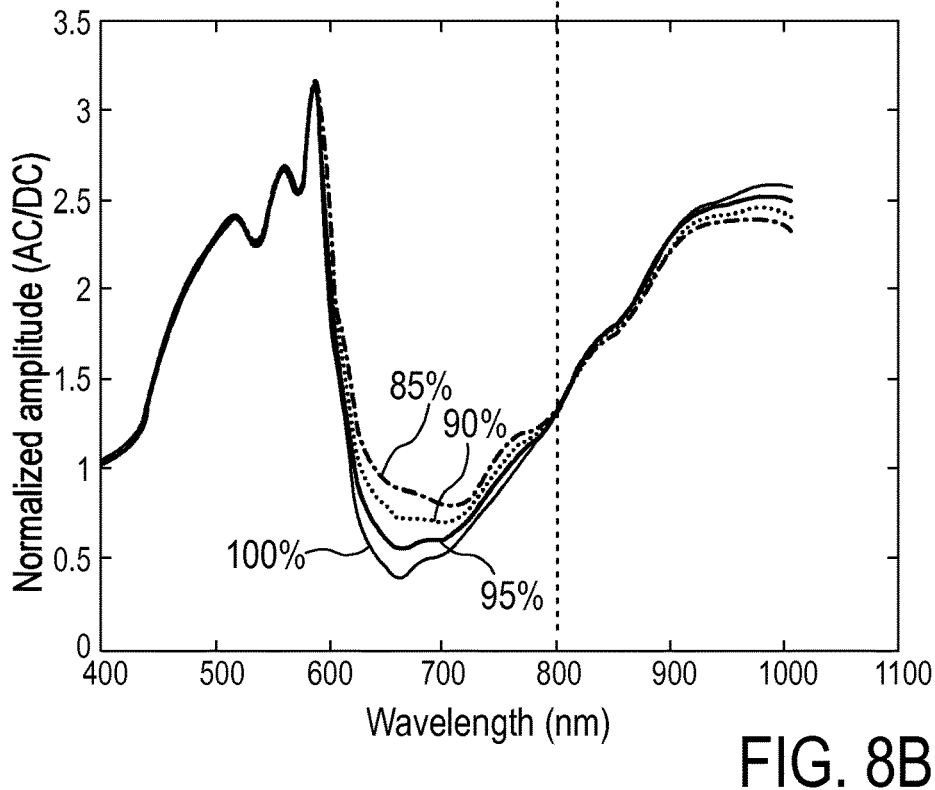

The present invention thus provides the option to build a very inexpensive camera for generating a biometrical signal of a living being, in particular of an SpO2 signal and/or heart rate signal. FIG. 8A show the sensitivity for the two combined color signals Ch1 and Ch2 as explained above, and FIG. 8B shows the PPG amplitude spectra as depicted in FIG. 7. As indicated by the vertical line through 800 nm the two combined color signals Ch1 and Ch2 are now near optimal SpO2 wavelength bands, similar to those as obtained in conventional pulse oximetry. As mentioned above, conventional pulse oximetry uses a red band (around 660 nm), where a significant difference in light absorption between oxy- and deoxyhemoglobin exists, and an infra-red band (850-940 nm), where this difference is much smaller and in the opposite direction. A wavelength of 800 nm is an isosbestic point of the hemoglobin, i.e. both oxy- and deoxyhemoglobin have the same light absorption.

As explained above a SpO2 signal is extracted from said at least one combined color signal by extracting at least two PPG signals at different wavelengths and determining a SpO2 signal from said at least two PPG signals.

Figure 9A:
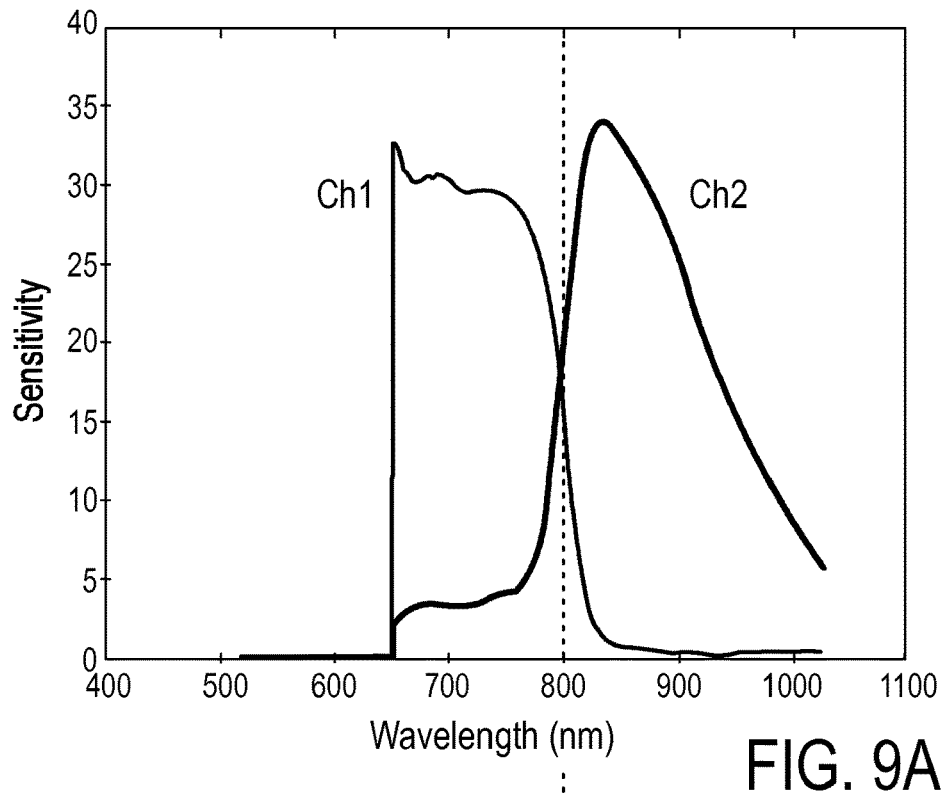
FIG. 9 shows diagrams for sensitivity and normalized amplitude illustrating HR signal evaluation.
Figure 9B:
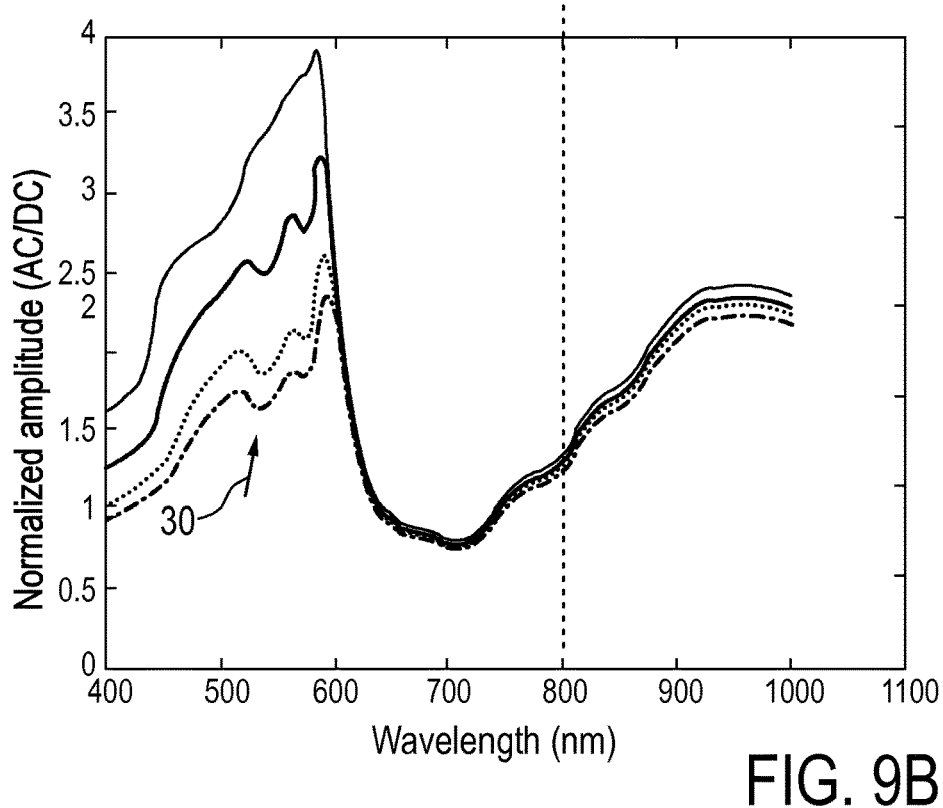

FIG. 9A also shows the two combined color signals Ch1, Ch2 as explained above, and FIG. 9B shows unstable PPG amplitudes due to variations between individuals in the visible wavelength range as indicated by arrow 30. The variations in the amplitude are for different individuals (different modeled skin physiologies) and not due to the oxygenations levels. As shown in these diagrams, for a simple detection of the heart rate a good stable contrast in amplitude between the two channels Ch1, Ch2 is desired as is given in this case. The conventionally used green wavelength range (500 to 600 nm) is strong in amplitude, but not stable. As explained above a conventional PPG extraction algorithm can be applied to the two channels to obtain a PPG signal representing the heartbeat signal.

Figure 10A:
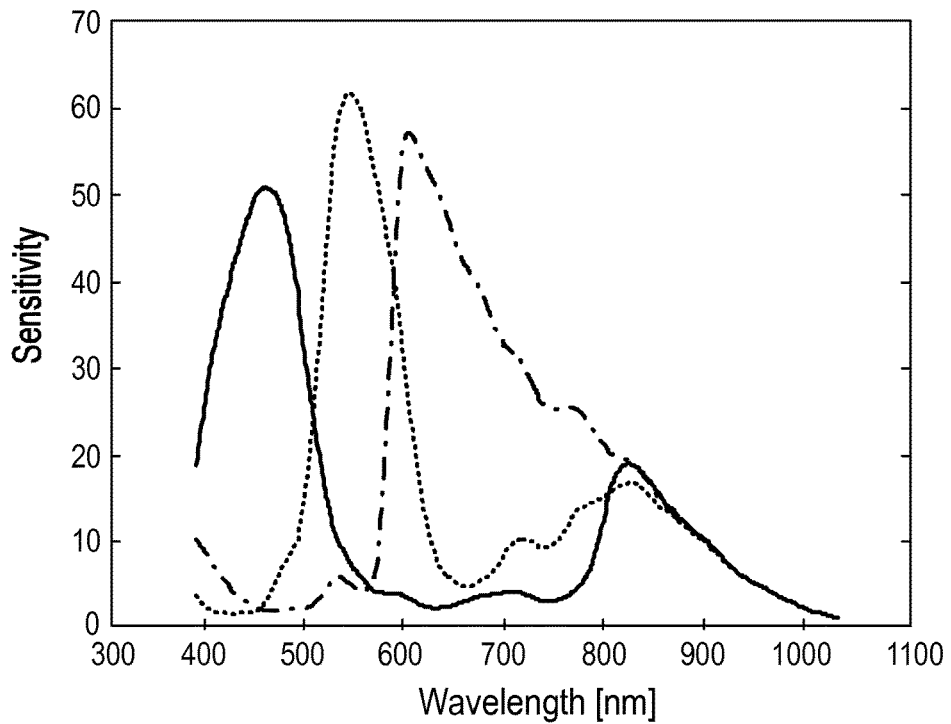
FIGS. 10A to 10C show diagrams of the sensitivity of another sensor without and with a filter for blocking visible light and of two combined color channels.
Figure 10B:
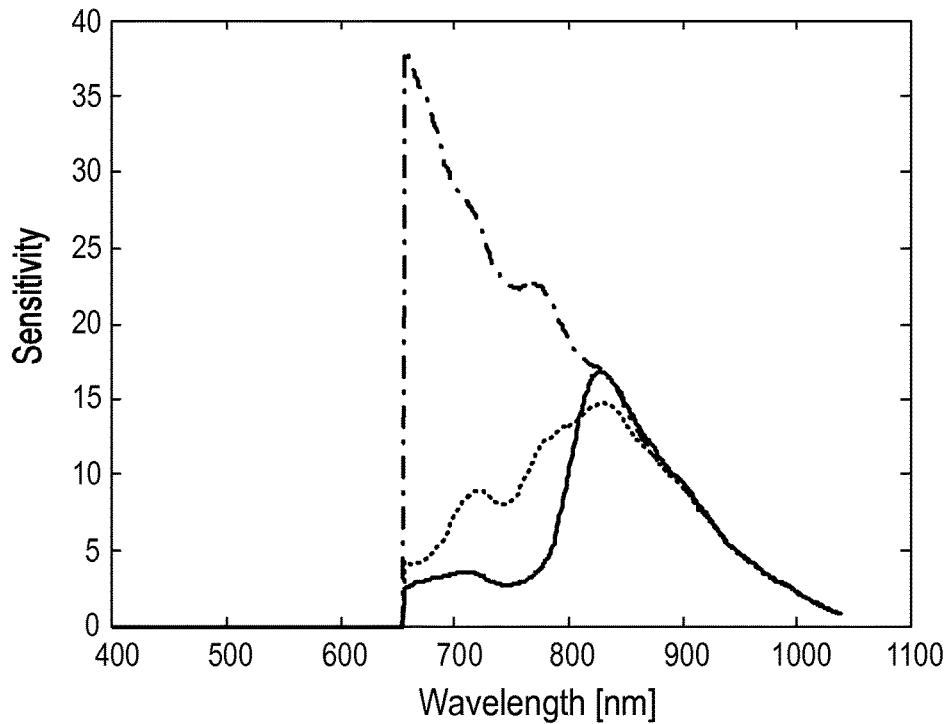
Figure 10C:
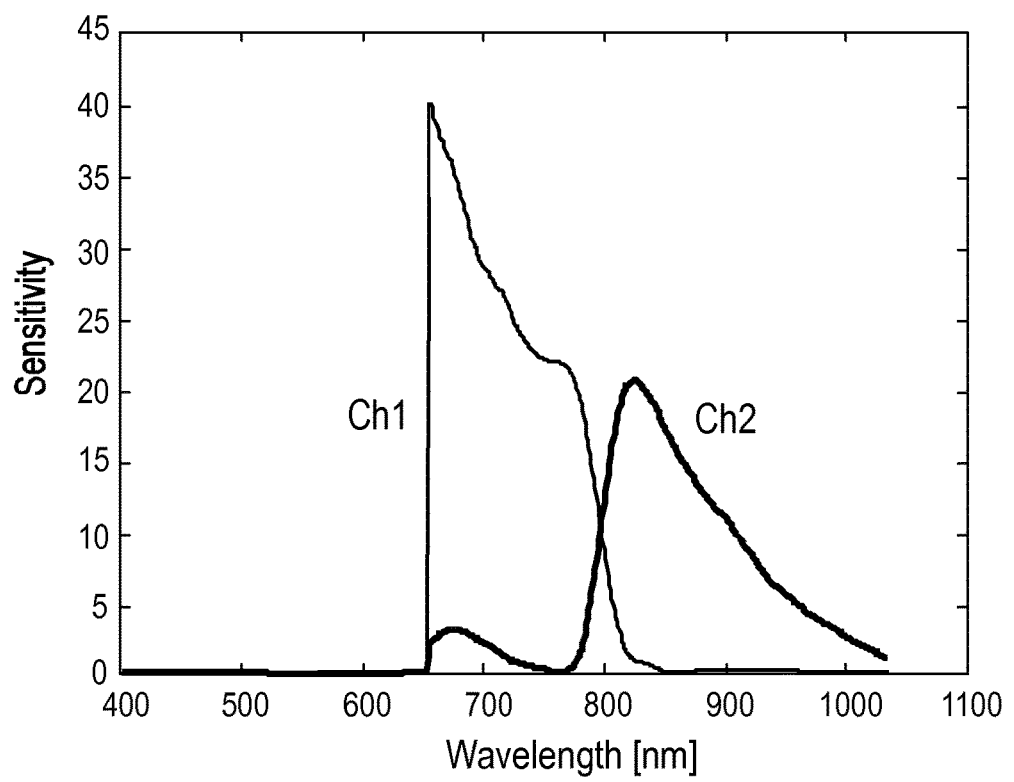

FIGS. 10A to 10C show corresponding diagrams for a different color sensor. FIG. 10A shows a diagram of the spectral characteristic of the color sensor and FIG. 10B shows a diagram of the spectral characteristic of said color sensor with a filter blocking visible light. FIG. 10C shows a diagram of the virtual color channels Ch1 and Ch2 resulting from a combination of RGB, where Ch1=R−B and Ch2=1.5*B−0.5*G.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A camera for generating a biometrical signal of a living being comprising:
   a filter configured to block incident visible light in a wavelength range up to at least 550 nm,
   a color sensor configured to receive said filtered incident light and configured to generate a red color signal, a green color signal and a blue color signal; and
   at least one processor programmed to:
      generate a first combined color signal by adding the red color signal and the green color signal and subtracting two times the blue color signal from said sum;
      generate a second combined color signal by subtracting the green color signal from two times the blue color signal;
      extract at least one biometrical signal of said living being from at least one of the first and second combined color signals.

2. The camera as claimed in claim 1, wherein said filter is adapted for blocking incident visible light in a wavelength range up to at least 650 nm.

3. The camera as claimed in claim 1, further comprising a second filter configured to block incident light in a wavelength range above at least 1100 nm, in particular above at least 1000 nm, before reaching said color sensor.

4. The camera as claimed in claim 1, wherein the at least one processor is further programmed to extract a SpO2 signal from said at least one combined color signal by extracting at least two PPG signals at different wavelengths and determining a SpO2 signal from said at least two PPG signals.

5. The camera as claimed in claim 1, wherein the at least one processor is further programmed to extract a heartbeat signal from said at least one combined color signal by PPG extraction.

6. A method for generating a biometrical signal of a living being comprising the steps of:
   with a filter, blocking incident visible light in a wavelength range up to at least 550 nm,
   with a color sensor, receiving said filtered incident light,
   with at least one processor, generating a red color signal, a green color signal and a blue color signal from the received filtered incident light,
   with the at least one processor, generating first and second combined color signals by (i) generating a first combined color signal by adding the red color signal and the green color signal and subtracting two times the blue color signal from said sum and (ii), generating a second combined color signal by subtracting the green color signal from two times the blue color signal; and
   with the at least one processor, extracting at least one biometrical signal of said living being from the first and second combined color signals.

7. The method as claimed in claim 6, further including:
   with the filter, blocking incident visible light in a wavelength range up to at least 650 nm.

8. The method as claimed in claim 6, further including:
   with a second filter, blocking incident light in a wavelength range above at least 1000 nm before reaching the color sensor.

9. The method as claimed in claim 6, further including:
   with the at least one processor, extracting a SpO2 signal from the at least one combined color signal by extracting at least two PPG signals at different wavelengths and determining a SpO2 signal from said at least two PPG signals.

10. A camera for generating a biometrical signal of a living being, the camera comprising:
    a filter configured to block incident visible light in a wavelength range up to at least 650 nm,
    a color sensor configured to receive the filtered incident light and configured to generate a red color signal, a green color signal and a blue color signal, and
    at least one processor programmed to:
       generate at least two combined color signals by making two different linear combinations of at least two of the red, green, and blue color signals, the at least two combined color signals including (i) a first combined color signal generated by adding the red color signal and the green color signal and subtracting two times the blue color signal from the sum; and (ii) a second combined color signal generated by subtracting the green color signal from two times the blue color signal, and
       extract a SpO2 signal of the living being from the at least two combined color signals by extracting at least two PPG signals at different wavelengths from the at least two combined color signals and determining a SpO2 signal from said at least two PPG signals.

* * * * *